(12) United States Patent
Lee

(10) Patent No.: US 7,670,540 B2
(45) Date of Patent: Mar. 2, 2010

(54) APPARATUS FOR MANUFACTURING BALLOON CATHETER AND METHOD THE SAME

(76) Inventor: Keun-Ho Lee, #2608-1204, Hayan-maeul Apt., 570-1, Sang-dong, Wonmi-gu, Bucheon-si, Gyeonggi-do (KR)

( * ) Notice: Subject to any disclaimer, the term of this patent is extended or adjusted under 35 U.S.C. 154(b) by 900 days.

(21) Appl. No.: 11/420,931

(22) Filed: May 30, 2006

(65) Prior Publication Data

US 2007/0006964 A1 Jan. 11, 2007

(30) Foreign Application Priority Data

Jun. 17, 2005 (KR) .................... 10-2005-0052449

(51) Int. Cl.
| | |
|---|---|
| B29C 35/08 | (2006.01) |
| B29C 47/00 | (2006.01) |
| B29C 47/60 | (2006.01) |
| B27B 17/00 | (2006.01) |
| B32B 33/00 | (2006.01) |
| A61M 29/00 | (2006.01) |

(52) U.S. Cl. ............... 264/400; 264/130; 264/132; 264/150; 264/151; 264/154; 264/156; 264/157; 264/171.12; 264/171.13; 264/171.26; 264/171.27; 264/173.11; 264/173.12; 264/173.16; 264/177.17; 264/177.19; 264/209.3; 264/209.4; 264/209.5; 264/210.2; 264/210.3; 264/211.12; 264/211.23; 264/294; 264/297.5; 264/347; 427/2.3; 604/96.01; 606/192; 606/194

(58) Field of Classification Search .................. None
See application file for complete search history.

(56) References Cited

U.S. PATENT DOCUMENTS

| 2,974,713 | A | * | 3/1961 | Hydrick, Jr. | ................ | 156/149 |
| 4,267,848 | A | * | 5/1981 | Rijckaert | ................ | 131/304 |
| 5,137,671 | A | * | 8/1992 | Conway et al. | ............. | 264/130 |
| 6,235,226 | B1 | * | 5/2001 | Lee | ............................. | 264/130 |
| 6,537,480 | B1 | * | 3/2003 | Becker et al. | ............... | 264/400 |
| 6,623,452 | B2 | * | 9/2003 | Chien et al. | ............ | 604/103.01 |
| 6,740,273 | B2 | * | 5/2004 | Lee | ............................. | 264/130 |

* cited by examiner

Primary Examiner—Jeffrey Wollschlager
(74) Attorney, Agent, or Firm—GWiPS

(57) ABSTRACT

Disclosed herein are an apparatus and method for manufacturing a balloon catheter in which a non-contact type laser perforator and printer are separately provided above a primary extruder such that inflation apertures can be uniformly perforated through a non-vulcanized lumen tube and simultaneously, tube cutting positions can be printed on the lumen tube at positions uniformly spaced apart from the inflation apertures without stopping a primary extrusion process. Also, a bond preventing agent layer is coated on the lumen tube at balloon inflating portions prior to cutting the tube, to facilitate a secondary extrusion of the tube. With this configuration, continuous and accurate perforation of inflation apertures is possible and automatic tube cutting can be achieved based on the printed tube cutting positions. Also, the present invention can compensate for a time delay due to a bond preventing agent application process and achieve high productivity and minimized loss of material.

2 Claims, 13 Drawing Sheets

APPARATUS FOR MANUFACTURING BALLOON CATHETER AND METHOD THE SAME

Pursuant to 35 U.S.C. § 119(a), this application claims the benefit of earlier filing date and right of priority to Korean Application No. 10-2005-0052449, filed on Jun. 17, 2005, the contents of which is hereby incorporated by reference herein in its entirety.

BACKGROUND OF THE INVENTION

1. Field of the Invention

The present invention relates to an apparatus and method for manufacturing a balloon catheter, and more particularly, to an apparatus and method for manufacturing a balloon catheter in which: a laser perforator and printer are separately provided above a T-shaped die of a primary tube extruder such that inflation apertures, each having a predetermined area and length, can be accurately and uniformly perforated through an elongated non-vulcanized lumen tube and tube cutting positions can be printed on the non-vulcanized tube without stopping a primary extrusion process; and a bond preventing agent layer is coated on an outer surface of the elongated lumen tube at balloon inflating portions prior to cutting the elongated lumen tube to facilitate the implementation of a secondary extrusion, whereby high productivity and minimized loss of material can be achieved.

2. Description of the Related Art

As known, a catheter, which is conventionally made of silicon, is a thin and long circular tube adapted to be inserted into the human body in order to drain a body fluid or to inject a therapeutic fluid. For instance, such a catheter may be used to drain urine. In this case, the catheter is inserted into the bladder through the urethra so as to drain urine collected in the bladder.

FIG. 1 is a sectional view illustrating a tip portion of a conventional balloon catheter.

As shown in FIG. 1, the conventional balloon catheter includes a lumen tube 13 formed with a partition 19 therein to define a primary lumen 12 and an inflation lumen 14, and a balloon layer 16 partially bonded to an outer surface of the lumen tube 13 to provide a balloon. The primary lumen 12 serves to drain urine introduced from the bladder through a urine drainage hole 17, whereas the inflation lumen 14 serves to inflate the balloon provided by the balloon layer 16. An inflation hole 15 is also formed at the lumen tube 13 in order to communicate the inflation lumen 14 with an interior space 16a of the balloon.

In order to manufacture the balloon catheter having the above mentioned configuration, an extrusion process is carried out to extrude an intermediate tube having the primary lumen 12 and inflation lumen 14. Thereafter, the extruded intermediate tube is primarily vulcanized, and then cut into tube pieces having a desired length, that is, lumen tubes 13.

Subsequently, the inflation hole 15 and urine drainage hole 17 are perforated through each lumen tube 13. A tip 11 is then formed at one end of each lumen tube 13. Thereafter, a balloon manufactured in a separate molding process is bonded, as the balloon layer 16, to the outer surface of each lumen tube 13 by an adhesive 18. Each lumen tube 13 is then subjected to an overcoating process to form an overcoat layer 20. The overcoating process is performed for the sake of removing any protrusions on the outer surface of each lumen tube 13.

In the above mentioned conventional balloon catheter, however, there is a problem in that it may cause a patient great pain during a surgical operation because its balloon-bonded portion has a diameter relatively larger than that of other portions. Furthermore, the bonded portions of the balloon may be separated. First of all, the conventional balloon catheter results in a complicated process and high manufacturing costs.

As a solution to eliminate the above mentioned problems of the conventional balloon catheter, another conventional catheter manufacturing method is disclosed in U.S. Pat. No. 5,137,671.

This method will be described hereinafter with reference to FIGS. 2A to 2E. First, a double lumen tube 100 is prepared, as shown in FIG. 2A. The double lumen tube 100 is formed with a first lumen 120 (a larger diameter fluid conduit lumen) and a second lumen 140 (a smaller diameter capillary lumen).

A capillary lumen access opening 160 is punched through the prepared lumen tube 100 at an intermediate portion of the lumen tube 100, that is, a balloon inflating portion, so that it communicates with the second lumen 140, as shown in FIG. 2B. The second lumen 140 is then filled with a polymeric filling material 180 such as silicon rubber between one end thereof (that is, the left end in FIG. 2B) and a point just before the capillary lumen access opening 160. A tip 200 is attached to one end of the lumen tube 100 corresponding to the end of the second lumen 140, so that both of the first and second lumens 120 and 140 are closed at one end thereof.

Subsequently, a portion of the lumen tube 100 extending from one end of the lumen tube 100 to the balloon inflating portion, that is, up to the line A-A in FIG. 2B, is dipped into a bond preventing agent solution (a liquid soap or petrolatum), and then dried, so that it is coated at an outer surface thereof with a solidified bond preventing agent layer 300. The bond preventing agent layer 300 fills the capillary lumen access opening 160 and a portion of the second lumen 140. Thus, the bond preventing agent layer 300 has a cross section as shown in FIG. 2B. That is, the portion of the second lumen 140 between the line A-A and the capillary lumen access opening 160 is filled with the bond preventing agent layer 300, and the outer surface portion of the lumen tube 100 between the line A-A and the end of the lumen tube 100 adjacent to the tip 200 is coated with the bond preventing agent layer 300, along with the tip 200, as shown in FIG. 2B.

Thereafter, a portion of the lumen tube 100 extending up to the line B-B in FIG. 2C, that is, just before the balloon inflating portion, is treated using a surface active agent, and then dipped into hot water or other hot aqueous solution several times, so as to remove the bond preventing agent layer 300 therefrom. Thus, the bond preventing agent layer 300 remains only at the balloon inflating portion of the lumen tube 100, as shown in FIG. 2C. A liquid-phase silicon is then coated over the entire outer surface of the lumen tube 100 to form a silicon layer 400, as shown in FIG. 2D. The silicon layer 400 may have a multi-layer structure including laminated layers 410 and 420.

Then, a solvent for melting and removing the bond preventing agent is injected into the second lumen 140 from the other end of the second lumen 140, so that the remaining bond preventing agent layer 300 filling and covering the balloon inflating portion is completely removed from the second lumen 140 of the lumen tube 100, thereby forming a balloon inflation cavity 440, as shown in FIG. 2E. Thus, a balloon catheter is obtained.

However, this balloon catheter manufacturing method has a problem in that it causes environmental pollution due to waste water produced during the procedure of dipping the lumen tube 100 into water several times in order to remove the bond preventing agent from the portion of the lumen tube 100 (between the line B-B and the tip-side end) other than the balloon inflating portion.

Furthermore, where the bond preventing agent is incompletely removed, the residue thereof is moved to the tip 200 when the balloon inflation cavity is inflated, thereby causing the overcoat layer to be stripped around the balloon inflating portion. As a result, the overcoat layer may be inflated around the balloon inflating portion.

Also, the above mentioned conventional balloon catheter manufacturing method still has the problem caused by the diameter of the balloon inflating portion being larger than that of other portions.

As another conventional example, there is a silicon rubber catheter disclosed in Japanese Utility Model No. 3015310 registered on Jun. 21, 1995.

In this catheter, a balloon is formed on the outer surface of a catheter body such that it is integral with the catheter body. The catheter body is formed using silicon rubber in accordance with a primary extrusion process so that it is defined with a fluid conduit lumen and a capillary lumen therein, and formed with a channel at the outer surface thereof. The catheter body is subjected to a vulcanization process, and then coated with a bond preventing agent at a balloon forming portion thereof. Thereafter, a balloon layer is laminated using silicon rubber over the outer surface of the catheter body in accordance with a secondary extrusion process, and then vulcanized. A tip is then formed at the catheter body. In this structure, the outer surface of the balloon layer is flush with the outer surface of the catheter body at the catheter body portion other than the balloon forming portion, so that there is no step formed at the outer surface of the catheter body. Accordingly, there is no resistance caused by steps, and no deformation in the outer surface of the balloon layer.

However, it is difficult to practically manufacture such a catheter, in which the balloon is integral with the catheter body.

This is because the silicon rubber layer coated in the secondary extrusion process may penetrate into the channel. Where the silicon rubber layer is coated without any penetration thereof into the channel, it is difficult to obtain a sufficient bonding force to the catheter body. In this case, the silicon rubber layer may be stripped even at a region other than the balloon forming portion. Furthermore, even if the secondary extrusion process is successfully accomplished with no stripping and penetration of the silicon rubber layer, it is very difficult to provide the inflated balloon with a symmetrical shape because the channel leaves a longitudinal mark at an inner surface of the balloon.

To solve the above mentioned problems, the applicant of the present invention filed a patent application entitled "METHOD FOR MAKING BALLOON CATHETER" on 2001. The filed patent was published as Patent Registration No. 10-0434720.

The method for making a balloon catheter disclosed in the Patent Registration No. 10-0434720 will be described with reference to FIGS. 3A to 3C. The disclosed method comprises the steps of: primarily extruding an elongated lumen tube provided with a fluid drainage lumen and an inflation lumen while having an outer diameter slightly smaller than that of a desired balloon catheter, vulcanizing the elongated lumen tube, and cutting the elongated lumen tube into unit lumen tubes respectively corresponding to the desired balloon catheter; fitting a support rod in the fluid drainage lumen of each unit lumen tube to extend up to a balloon forming region where a balloon is to be formed on the unit lumen tube, and perforating two inflation apertures having a small diameter through the unit lumen tube at the balloon forming region; coating a bond preventing agent on an outer surface of each unit lumen tube at the balloon forming region; removing the support rod from each unit lumen tube, connecting the unit lumen tubes in series by connectors, secondarily extruding a balloon tube on the connected unit lumen tubes, vulcanizing the balloon tube, and cutting a resulting tube structure obtained after the vulcanization of the balloon tube into tube pieces respectively corresponding to the unit lumen tubes; forming a tip at one end of each tube piece; and perforating a urine drainage hole through each tube piece.

The above mentioned method, however, has the following several problems Firstly, as shown in FIG. 3C, since it is necessary to reduce a thickness ta of the lumen tube as thin as possible in order to increase the size of the fluid drainage lumen 12 and inflation lumen 14 to the maximum extent, perforation of the inflation apertures is very difficult, and such a difficulty may result in deterioration of productivity and increased amount of poor products. Secondly, where the inflation apertures are manually perforated through the lumen tube by use of elongated tools having a rod shape, the lumen tube must be cut prior to perforating the inflation apertures, for the sake of handling convenience. In this case, the lumen tube must be cut such that each unit lumen tube has a length longer than a desired length of the balloon catheter in consideration of the following processes, and the unit lumen tube must be cut again to have an accurate length after a secondary extrusion process. Accordingly, loss of material and excessive waste of labor are inevitable. Thirdly, if the thickness ta of the lumen tube is excessively thin, the inflation apertures may be perforated to extend up to unintentional positions or the lumen tube may be unintentionally stretched rather than being perforated with the inflation apertures. However, thickening the lumen tube to some extent in order to prevent the above problems of the excessively thin thickness must worsen abrasion of a cutting blade. This may result in deterioration of productivity due to frequent exchange of blades. For these reasons, although it is well known that it is better to reduce the thickness of the lumen tube as thin as possible, there is a limit to practically reduce the thickness of the lumen tube.

SUMMARY OF THE INVENTION

The present invention has been made in view of the above mentioned problems, and an object of the invention is to provide an apparatus and method for manufacturing a balloon catheter in which: a laser perforator is separately provided above a T-shaped die of a primary extruder such that inflation apertures having a predetermined area and length can be uniformly perforated, in a non-contact manner, through an elongated non-vulcanized lumen tube at balloon inflating portions of the lumen tube during a primary extrusion process; a printer is separately provided just above the perforator such that tube cutting positions can be printed, in a non-contact manner, on the non-vulcanized lumen tube simultaneously with the perforation of the inflation apertures without stopping the primary extrusion process; a bond preventing agent layer is coated on an outer surface of the lumen tube at the balloon inflating portions prior to cutting the lumen tube to facilitate the implementation of a secondary extrusion process; and cutting of the lumen tube can be automatically performed after completing the secondary extrusion process and primary curing process, whereby high productivity and minimized loss of material can be achieved, and rapid and accurate manufacture of the desired balloon catheter is possible.

In accordance with an aspect of the present invention, this object is accomplished by providing an apparatus for manufacturing a balloon catheter comprising: a primary extruder having a T-shaped die adapted to primarily extrude an elongated lumen tube upward in a vertical direction; a laser perforator provided above the T-shaped die of the primary extruder and adapted to successively perforate inflation apertures through the non-vulcanized lumen tube at an interval of approximately 37 cm in a non-contact manner, each inflation aperture having a width of 0.3 mm and a length of 2 to 3 mm; a printer spaced apart upward from the laser perforator by a predetermined distance and adapted to print tube cutting positions on the non-vulcanized lumen tube in a non-contact manner, simultaneously with the perforation of the inflation apertures; a primary vulcanizer provided above the printer and adapted to perform a primary vulcanization process by use of a vertically extending hot air vulcanizing vessel (HAV) thereof; a drawer provided above the primary vulcanizer and having drawing and guide rollers; a bond preventing agent applicator tube feeding rollers provided at a side of the drawer and adapted to intermittently feed the primarily vulcanized lumen tube into a bond preventing agent applicator while repeatedly stopping and resuming the feeding of the lumen tube in cooperation with a heating/transfer device; the bond preventing agent applicator provided at a side of the bond preventing agent applicator tube feeding rollers and adapted to uniformly coat a bond preventing agent layer on an outer peripheral surface of the lumen tube, which was primarily vulcanized, at positions of the inflation apertures; the heating/transfer device provided at a side of the bond preventing agent applicator and adapted to dry the lumen tube with hot air having a temperature of approximately 150° C., the heating/transfer device having a transfer roller to intermittently transfer the lumen tube to a secondary extruder tube feeding roller while stationary drooping the lumen tube several times; the secondary extruder tube feeding roller provided at a side of the heating/transfer device and adapted to continuously feed the lumen tube to a secondary extruder while stationary drooping the lumen tube several times between the heating/transfer device and the secondary extruder, in order to allow the secondary extruder to continuously perform a secondary extrusion process even though the lumen tube is intermittently fed from the heating/transfer device; the secondary extruder adapted to continuously perform the secondary extrusion process for the lumen tube; a vertically extending primary curing device provided below the secondary extruder and adapted to perform a primary curing process for the secondarily extruded lumen tube; a cutter adapted to uniformly cut the lumen tube, having passed through the secondary extrusion and primary curing processes, into tube pieces, based on the tube cutting positions, each tube piece having a length suitable for forming a tip at one end thereof; and a plurality of plastic tip molds adapted to receive liquid-phase silicon rubber (LSR) for use in the forming of the tip at the end of each tube piece and a tip mold supporting plastic panel having a plurality of holes perforated therethrough to receive the tip molds therein, respectively.

In accordance with another aspect of the present invention, there is provided a method for manufacturing a balloon catheter comprising the steps of: primarily extruding an elongated lumen tube upward in a vertical direction by use of a T-shaped die provided in a primary extruder; perforating inflation apertures through the non-vulcanized lumen tube at an interval of approximately 37 cm by use of a non-contact type laser perforator provided above the T-shaped die of the primary extruder, each inflation aperture having a width of 0.3 mm and a length of 2 to 3 mm; printing tube cutting positions on the non-vulcanized lumen tube at positions uniformly spaced apart from the inflation apertures by use of a non-contact type printer provided above the laser perforator, simultaneously with the perforation of the inflation apertures; primarily vulcanizing the lumen tube, having passed through the perforation and printing processes, by use of a primary vulcanizer provided above the printer; drawing the lumen tube by use of a drawer including drawing and guide rollers, in order to prepare a primary curing of the lumen tube; stationary drooping the drawn lumen tube at a position just before a bond preventing agent applicator and intermittently feeding the lumen tube whenever the bond preventing agent applicator completes a foregoing bond preventing agent coating operation; uniformly coating a bond preventing agent layer on an outer peripheral surface of the lumen tube over the inflation apertures; drying the lumen tube, which was completely coated with the bond preventing agent layer using the bond preventing agent applicator, with hot air having a temperature of approximately 150° C., and intermittently transferring the dried lumen tube to a secondary extruder tube feeding roller; secondarily extruding the dried lumen tube by use of the secondary extruder if the lumen tube is fed to the second extruder after being stationary dropped several times via the second extruder tube feeding roller; primarily curing the secondarily extruded lumen tube by use of a primary curing device provided below the secondary extruder; uniformly cutting the lumen tube, having passed through the secondary extrusion and vulcanization processes, to tube pieces by use of a tube cutter based on the printed tube cutting positions of the lumen tube, each tube piece having a length suitable for forming a tip at one end thereof; forming a tip at one end of each tube piece by dipping the end of the tube piece into liquid-phase silicon rubber (LSR) while applying a negative pressure to an inflation lumen of each tube piece; and secondarily vulcanizing the tube pieces, each formed with the tip, at a temperature of approximately 125° C. for approximately 25 minutes, and perforating a urine drainage hole through each tube piece.

Preferably, an extruding speed of the secondary extrusion process may be equal to or faster than that of the primary extrusion process.

BRIEF DESCRIPTION OF THE DRAWINGS

The above objects, and other features and advantages of the present invention will become more apparent after a reading of the following detailed description when taken in conjunction with the drawings, in which.

DESCRIPTION OF THE PREFERRED EMBODIMENTS

Now, the present invention will now be described in detail with reference to the accompanying drawings.

Figure 4:
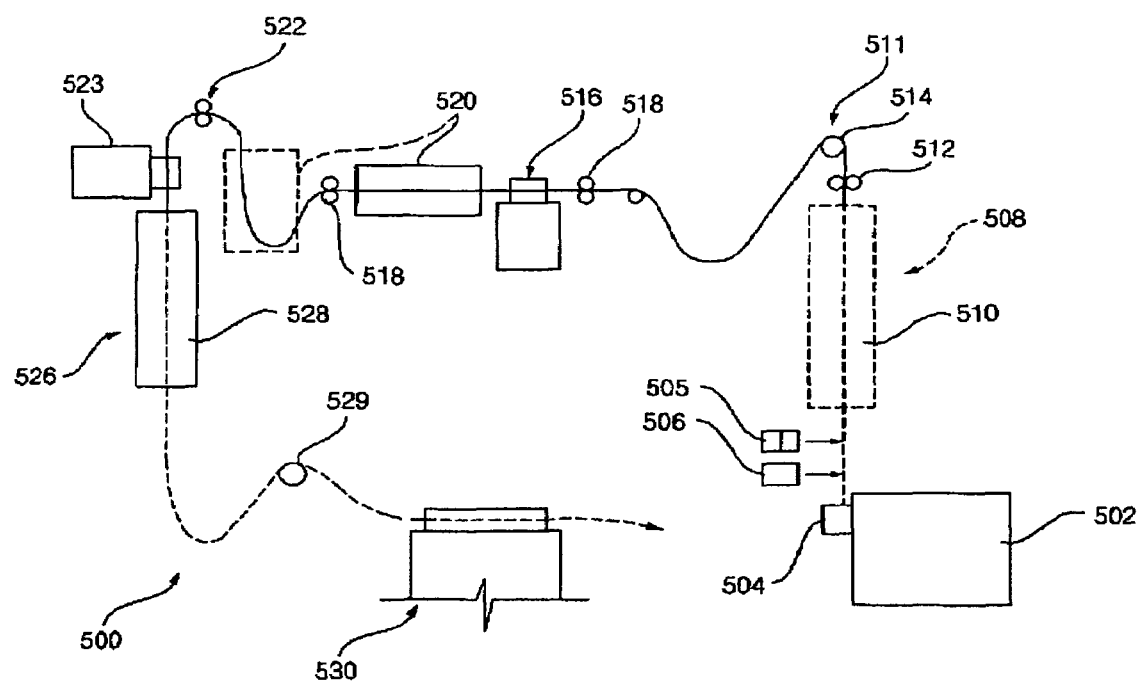
FIG. 4 is a schematic diagram illustrating an apparatus for manufacturing a balloon catheter in accordance with an embodiment of the present invention.
Figure 7:
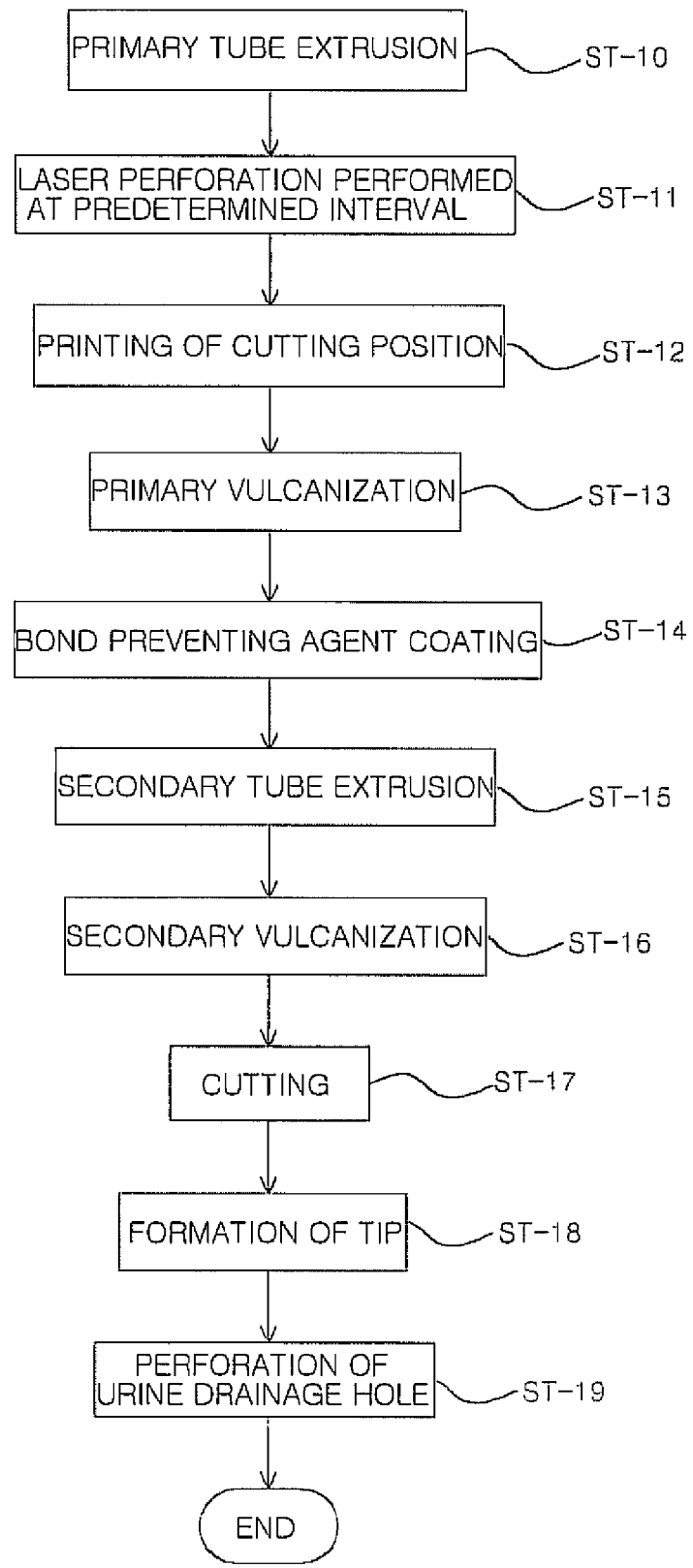
FIG. 7 is a flow chart illustrating sequential steps of a method for manufacturing a balloon catheter using the balloon catheter manufacturing apparatus in accordance with the embodiment of the present invention.

FIG. 4 is a schematic diagram illustrating an apparatus for manufacturing a balloon catheter in accordance with an embodiment of the present invention. FIG. 7 is a flow chart illustrating sequential steps of a method for manufacturing a balloon catheter using the balloon catheter manufacturing apparatus in accordance with the embodiment of the present invention.

As shown in FIG. 4, considering the balloon catheter manufacturing apparatus 500 in accordance with the embodiment of the present invention, a laser perforator and printer are provided above a T-shaped die of a primary extruder. With this arrangement, during a primary extrusion process, inflation apertures, each having a predetermined area and length, can be accurately and uniformly perforated, in a non-contact manner, through an elongated non-vulcanized lumen tube, and tube cutting positions can be printed on the non-vulcanized lumen tube without stopping the primary extrusion process. In the balloon catheter manufacturing apparatus 500, also, a bond preventing agent is applied to an outer surface of the elongated lumen tube at balloon inflating portions and then dried, prior to cutting the elongated lumen tube. This has the effect of achieving high productivity in association with a secondary extrusion process and minimizing loss of material. As a result, rapid manufacture of the balloon catheter is possible.

Specifically, in the balloon catheter manufacturing apparatus 500 in accordance with the embodiment of the present invention, an elongated lumen tube is extruded by use of a primary extruder 502 (Step ST-10). Conventionally, horizontal extruders have been used in a tube extrusion process and vulcanization process. However, the horizontal extruder has a problem in that they may remain fine contact traces at a surface of the extruded tube. For this reason, in the present invention, the primary extruder 502 takes the form of a vertical extruder in order to remain no trace at the surface of the extruded tube, and consequently, to prevent distortion of the extruded tube.

If the elongated lumen tube is extruded by use of a T-shaped die 504 of the vertical primary extruder 502, a laser perforator 506, which is arranged above an upper end of the T-shaped die 504, is operated to perforate inflation apertures (designated as reference numeral 23 in FIG. 6) through the lumen tube, which was completely extruded, at balloon inflating portions of the lumen tube (Step ST-11). The laser perforator 506 is able to continuously perforate the inflation apertures 23, each having a desired accurate area and length, through the non-vulcanized lumen tube at a predetermined interval (for example, a distance of 37 cm). Also, the laser perforator 506 is a non-contact type suitable to accurately perforate the inflation apertures 23 even when a thickness of the extruded lumen tube is very thin. In the present embodiment, the laser perforator 506 is preset to perforate an inflation aperture having a width of 0.3 mm and a length of 2 to 3 mm.

Here, a laser projecting time and projecting interval of the laser perforator 506 is automatically adjustable in accordance with an extruding speed of the primary extruder 502.

While the laser perforator 506 performs the inflation aperture perforation operation, a printer 505, which is upwardly spaced apart from the laser perforator 506 by a predetermined distance of approximately 4 to 5 cm, is operated to print tube cutting positions on the non-vulcanized lumen tube in a non-contact manner at positions uniformly spaced apart from the inflation apertures (Step ST-12). The printing of each tube cutting position is simultaneously performed with the perforation of each inflation aperture.

The non-vulcanized lumen tube, having passed through the perforation and printing processes, is guided to a primary vulcanizer 508 arranged above the laser perforator 506 and printer 505. The primary vulcanizer 508 includes a vertically extending hot air vulcanizing vessel (HAV) 510 for performing a primary vulcanization process for the extruded lumen tube (Step ST-13)

Provided above the HAV 510 is a drawer 511 including drawing and guide rollers 512 and 514. The primarily vulcanized tube is cooled to an appropriate temperature of 50 to 80° C. while passing through the drawer 511. Subsequently, a bond preventing agent layer having a predetermined width is uniformly coated to an outer peripheral surface of the drawn lumen tube at positions of the inflation apertures 23 (Step ST-14). The coating of the bond preventing agent layer is horizontally performed while passing through a bond preventing agent applicator 516. At a position just before the bond preventing agent applicator 516 are provided a tube feeding roller 51B for temporarily stopping the feeding of the lumen tube during a foregoing coating period and resuming the feeding of the lumen tube after the expiration of the foregoing coating period.

Accordingly, when the lumen tube is being guided from the drawer 511 to the bond preventing agent applicator 516, the drawn lumen tube is temporarily stopped while being drooped between the guide roller 514 of the drawer 511 and the tube feeding roller 518 for the bond preventing agent applicator 516, prior to being again fed to the bond preventing agent applicator 516.

This is because the advance of the lumen tube is temporarily stopped during the operation of the bond preventing agent applicator 516, but the drawing and guide rollers 512 and 514 of the primary extrusion drawer 511 continuously perform the tube drawing operation. Therefore, the lumen tube is remained stationary while being drooped between the tube feeding roller 518 and the drawer 511 such that a predetermined is length of the lumen tube can be fed into the bond preventing agent applicator 516 whenever the coating operation of the bond preventing agent applicator 516 is completed. Such an intermittent tube feeding operation will be repeatedly performed until the bond preventing agent layer is boated over all the inflation apertures 23.

After completion of the bond preventing agent layer using the bond preventing agent applicator 516, the lumen tube is guided to pass through a heating/transfer device 520 behind the bond preventing agent applicator 516. The heating/transfer device 520 is adapted to transfer the lumen tube while heating the lumen tube with hot air having a temperature of approximately 150° C. in order to dry the lumen tube via evaporation of moisture. This operation of the heating/transfer device 520 is closely connected with the foregoing intermittent bond preventing agent coating operation. Accordingly, a transfer roller (not shown) provided in the heating/transfer device 520 is not operated during the bond preventing agent coating operation, and then resume to transfer the lumen tube only when the tube feeding roller 518 operates. With this operation, the lumen tube is horizontally maintained in the bond preventing agent applicator 516.

A secondary extruder 523 having a tube feeding roller 522 is provided behind the heating/transfer device 520 for performing a secondary extrusion process (Step ST-15). The tube feeding roller 522 of the secondary extruder 523 are adapted to continuously feed the lumen tube coated with the bond preventing agent layer. However, since the lumen tube is intermittently fed from the heating/transfer device 520, the lumen tube is dropped between the heating/transfer device 520 and the tube feeding roller 522, in the same manner as between the tube feeding roller 518 and the primary extrusion drawer 511.

The secondary extrusion process is a process for laminating a silicon rubber balloon layer over the outer peripheral surface of the primarily extruded lumen tube having passed through the inflation aperture perforation, tube cutting position printing, primary vulcanization, and bond preventing agent coating and drying processes. After the secondary extrusion process is performed by the secondary extruder 523, the lumen tube is guided to a curing device 526 arranged below the secondary extruder 523. Thereby, the lumen tube is cured while passing through a hot air curing vessel 528 of the curing device 526 (Step ST-16). Meanwhile, the tube extruding speed of the secondary extruder 523 must be equal to or faster than that of the first extruder 502. If the extruding speed of the secondary extruder 523 fails to satisfy the above condition, namely, is slower than that of the first extruder 502, the operation of the secondary extruder 523 must be stopped intermittently such that a sufficient length of the lumen tube is placed between the tube feeding roller 522 and the heating/transfer device 520. Thereafter, the extruding speed of the secondary extruder 523 is gradually increased until it reaches an appropriate level.

After completing the second extrusion, the lumen tube, which was cured, is introduced into a tube cutter 530 by way of a secondary extrusion drawer 529. Thereby, as an optical sensor (not shown) attached to the cutter 530 senses the tube cutting positions printed on the lumen tube right after the primary extrusion process, the lumen tube is automatically cut to tube pieces based on a preset condition (Step ST-17).

Figure 5:
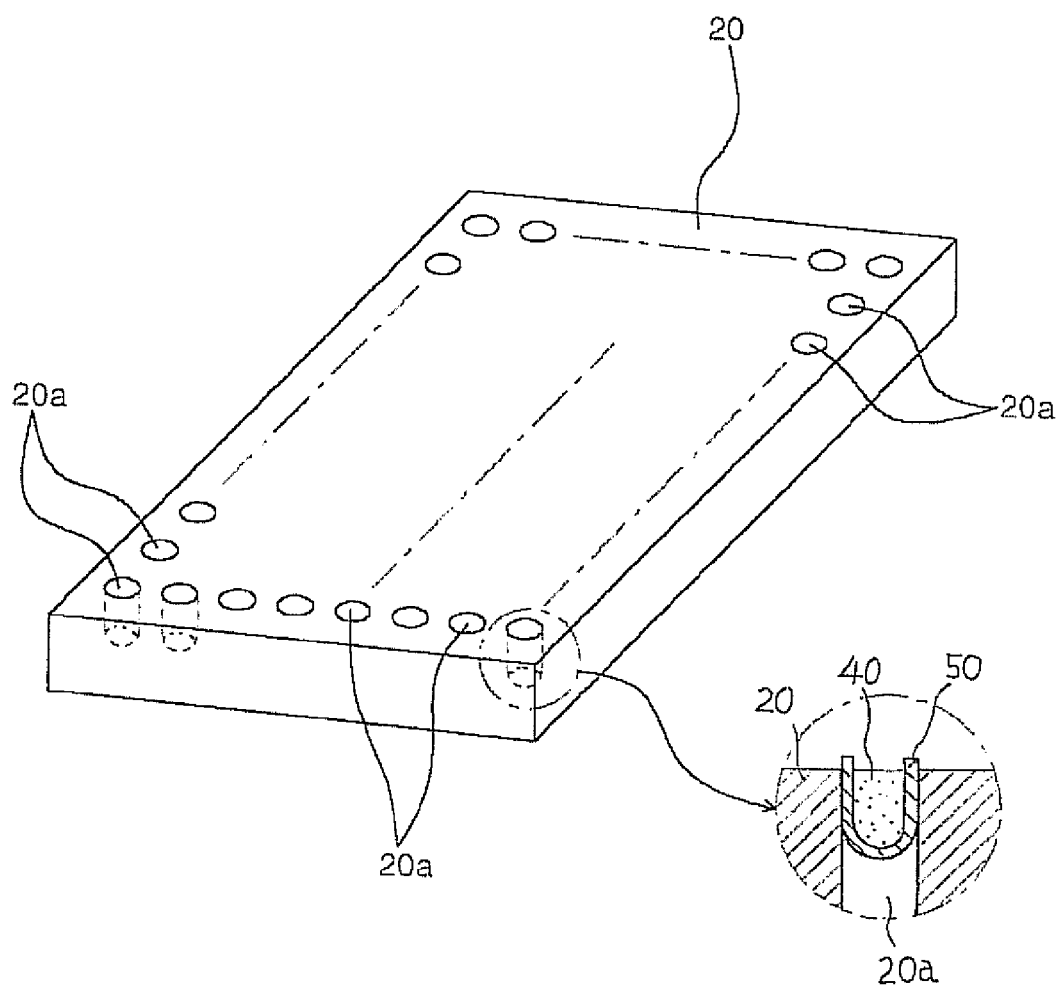
FIG. 5 is a perspective view illustrating a device and mold for use in a tip forming process, which are provided in the balloon catheter manufacturing apparatus in accordance with the embodiment of the present invention.
Figure 6:
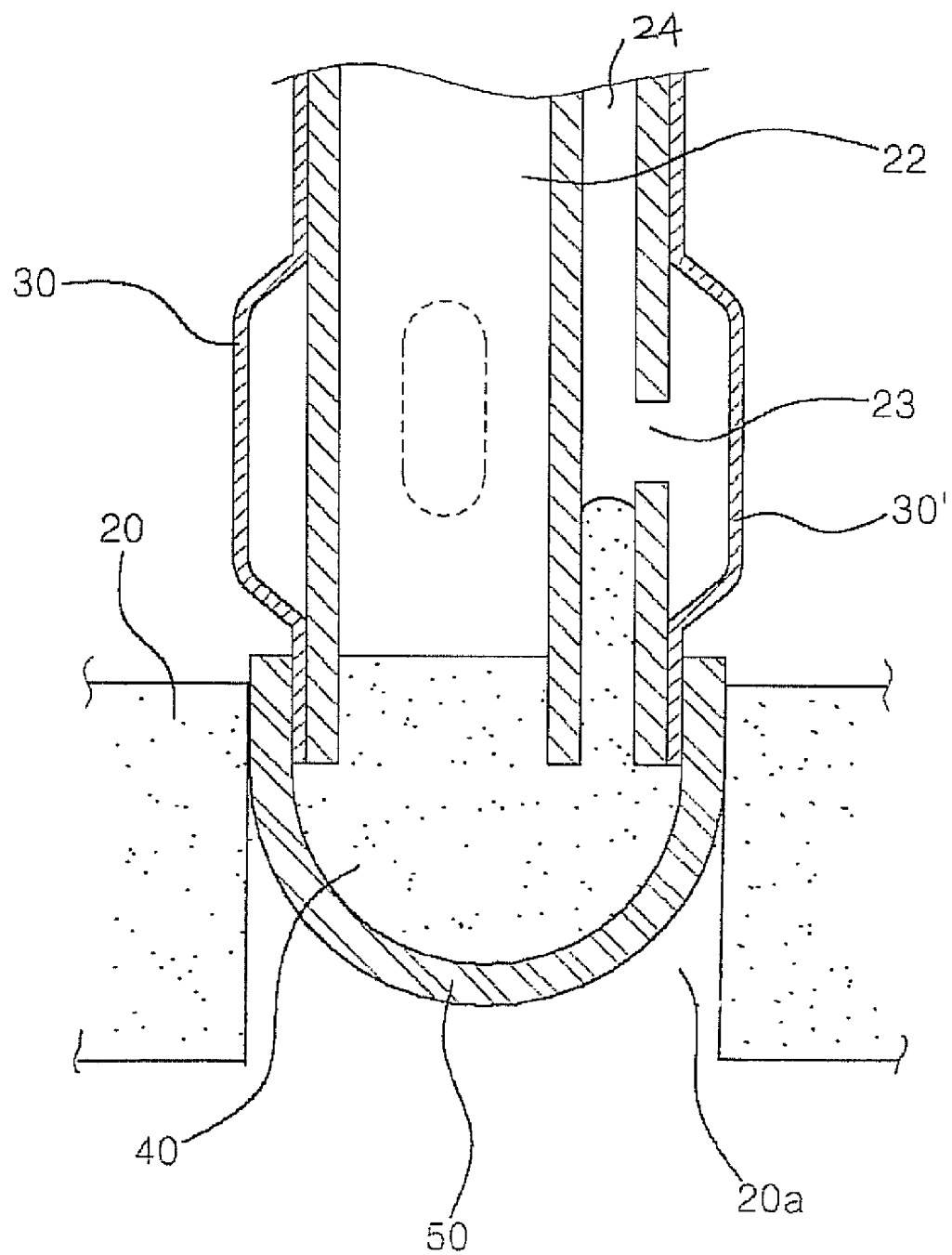
FIG. 6 is a detailed view illustrating a tip forming device of the balloon catheter manufacturing apparatus in accordance with the embodiment of the present invention.

FIG. 5 is a perspective view illustrating a device and mold for use in a tip forming process, which are provided in the balloon catheter manufacturing apparatus in accordance with the embodiment of the present invention. FIG. 6 is a detailed view illustrating a tip forming device of the balloon catheter manufacturing apparatus in accordance with the embodiment of the present invention.

Referring to the above drawings, after the elongated lumen tube, which was secondarily extruded and cured, is uniformly cut into tube pieces in the tube cutter 530 such that each tube piece has a length suitable for forming a tip at an end thereof (Step ST-17), one end of each tube piece is dipped into a plastic tip mold 50 which was previously filled with liquid-phase silicon rubber (LSR) 40 as shown in FIG. 5. Then, is if each tube piece is secondarily vulcanized, the forming of the tip is completed (Step ST-18).

Explaining the above mentioned tip forming process in detail, a tip mold supporting plastic panel 20 having a thickness of approximately 2 cm is prepared. The tip mold supporting plastic panel 20 has a plurality of holes 20a (each having a diameter smaller than 1 cm) uniformly perforated therethrough. If the tip mold supporting plastic panel 20 is prepared, plastic tip molds 50 are vertically inserted, respectively, into the holes 20a. Thereafter, a predetermined amount of liquid-phase silicon rubber 40 is automatically injected into each tip mold 50 by use of a dispenser (not shown) based on preset injection conditions. In this way, a plurality of tip molds 60 filled with the liquid-phase silicon rubber 40 are prepared such that they can be picked out of the tip mold supporting plastic panel 20 one by one whenever each tube piece is discharged from the tube cutter 530. If each tip mold 50 is picked out of the tip mold supporting plastic panel 20, one end of each tube piece near a balloon inflation portion is dipped into the liquid-phase silicon rubber 40 filled in each tip mold 50, and a connector such as an injector needle is inserted into the other end of each tube piece, more particularly, into an inflation lumen 24 of the tube piece. Then, if a negative pressure is applied into the inflation lumen 24, the liquid-phase silicon rubber 40 is drawn up to a point just below the inflation aperture 23. If ten to twenty tube pieces having passed through the above liquid-phase silicon rubber drawing process are gathered, they are simultaneously put into a vulcanizer (not shown) such that they can be vulcanized at a temperature of approximately 125° C. for approximately 25 minutes. Thereafter, if the tip mold 50 is removed from each tube piece, the tip forming process is completed (Step ST-18).

Figure 1:
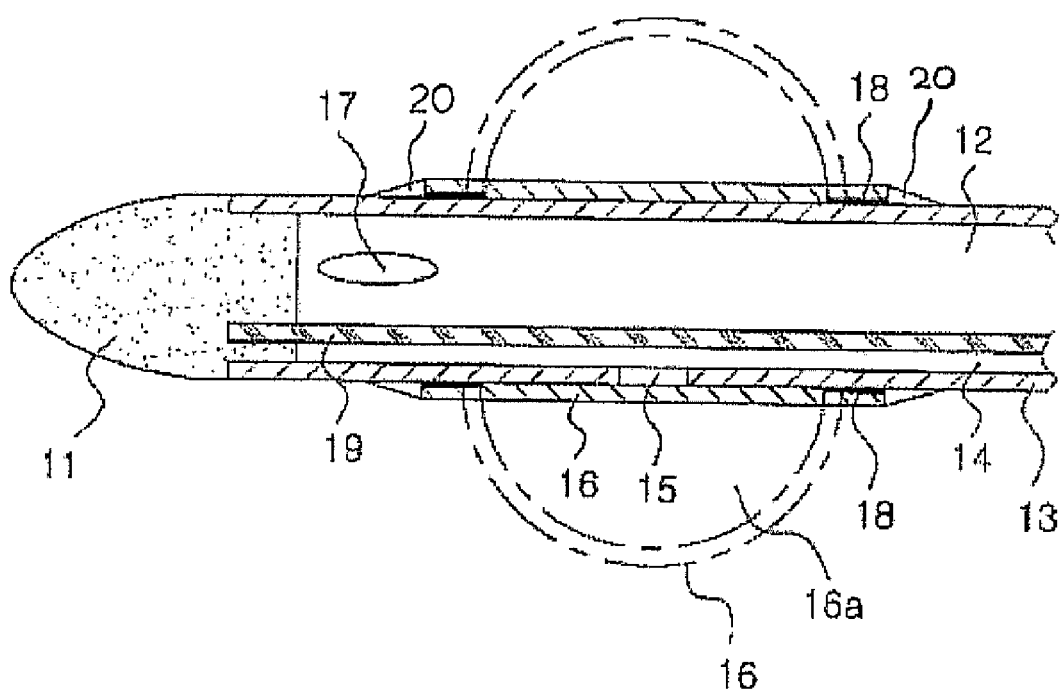
FIG. 1 is a sectional view illustrating a conventional balloon catheter.
Figure 2A:
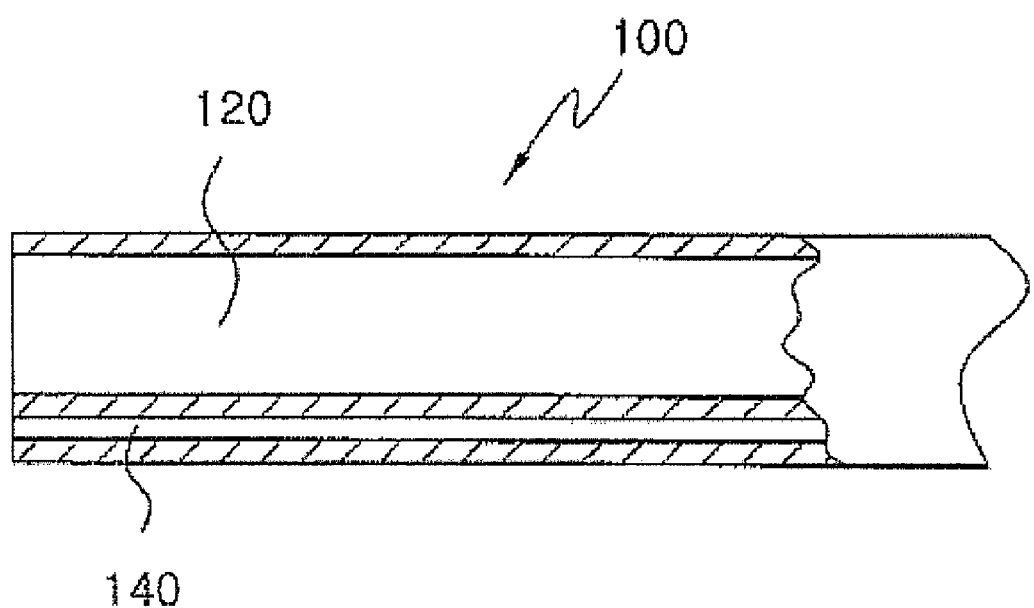
FIGS. 2A to 2E are sectional views respectively illustrating sequential steps of a conventional method for manufacturing a balloon catheter.
Figure 2B:
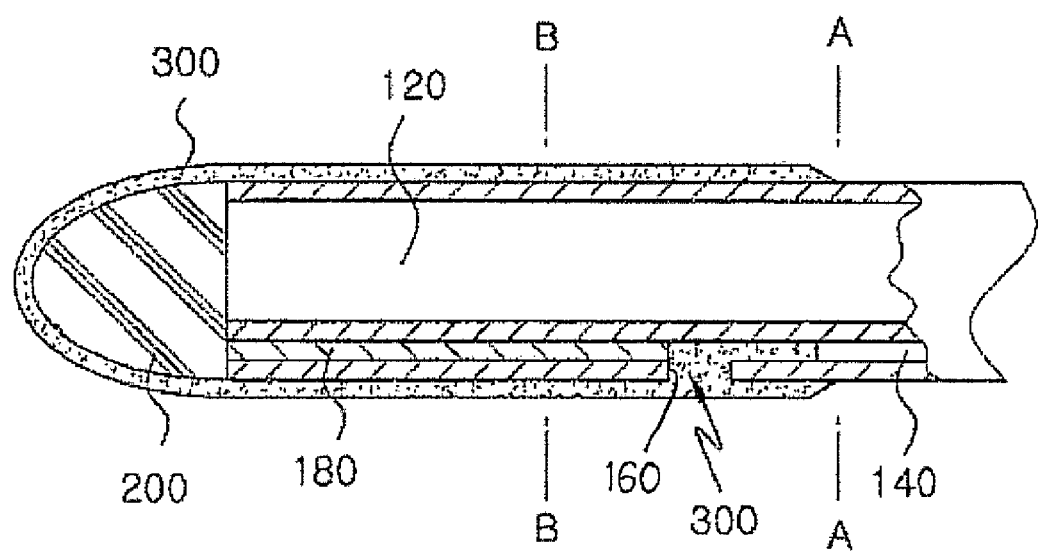
Figure 2C:
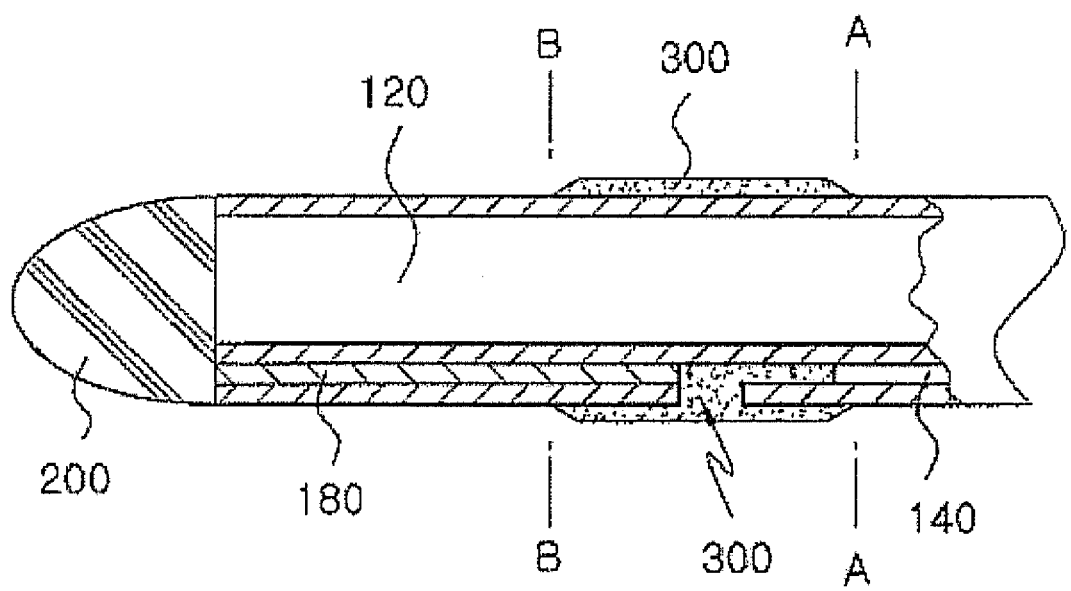
Figure 2D:
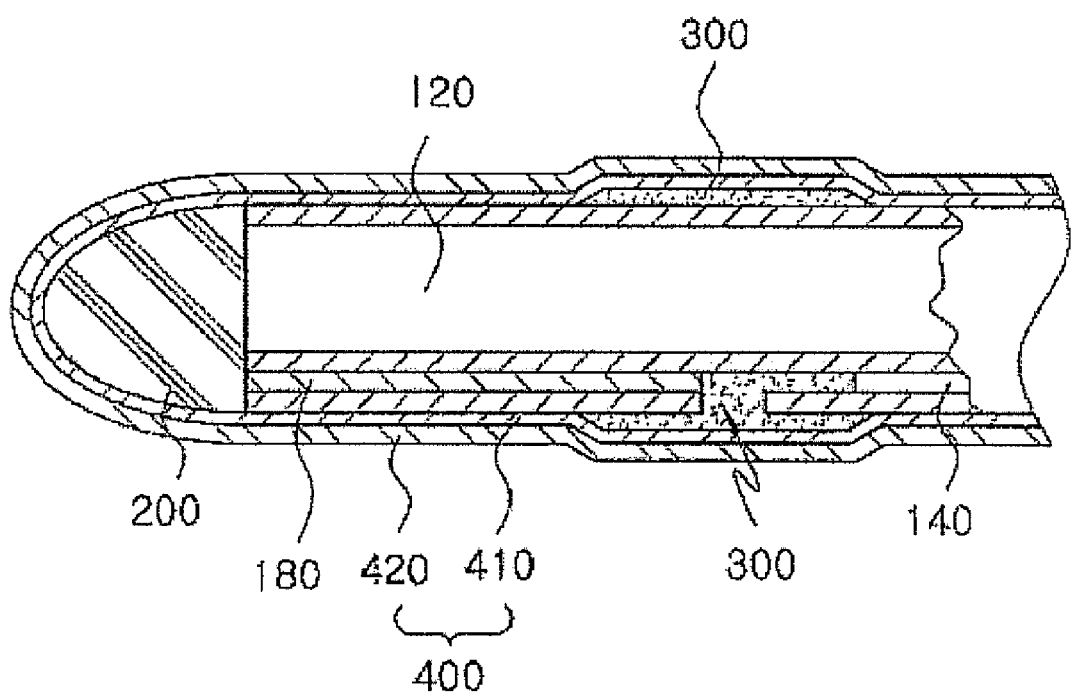
Figure 2E:
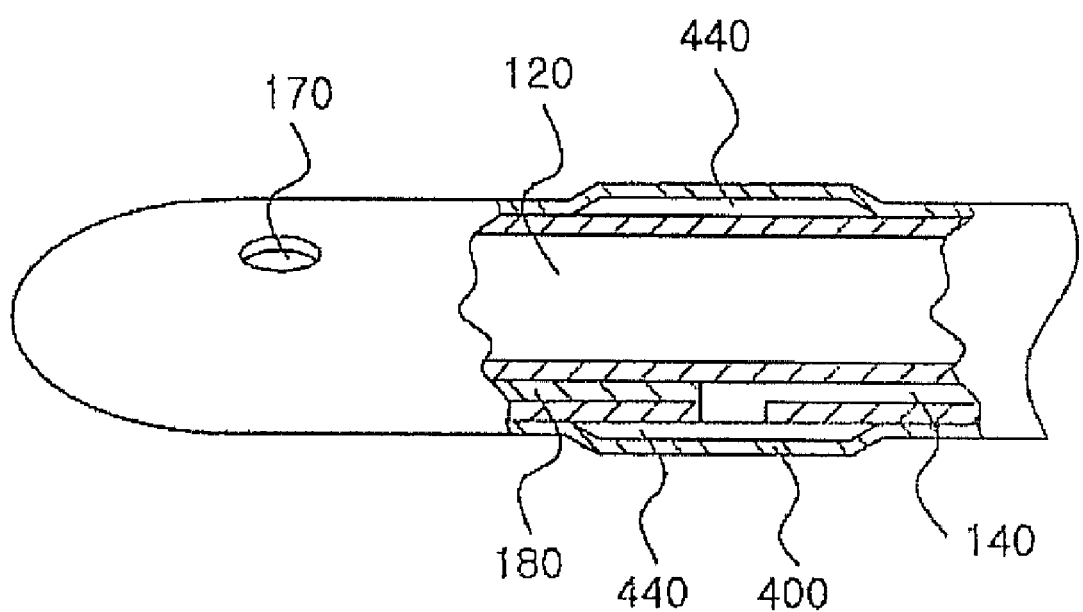
Figure 3A:
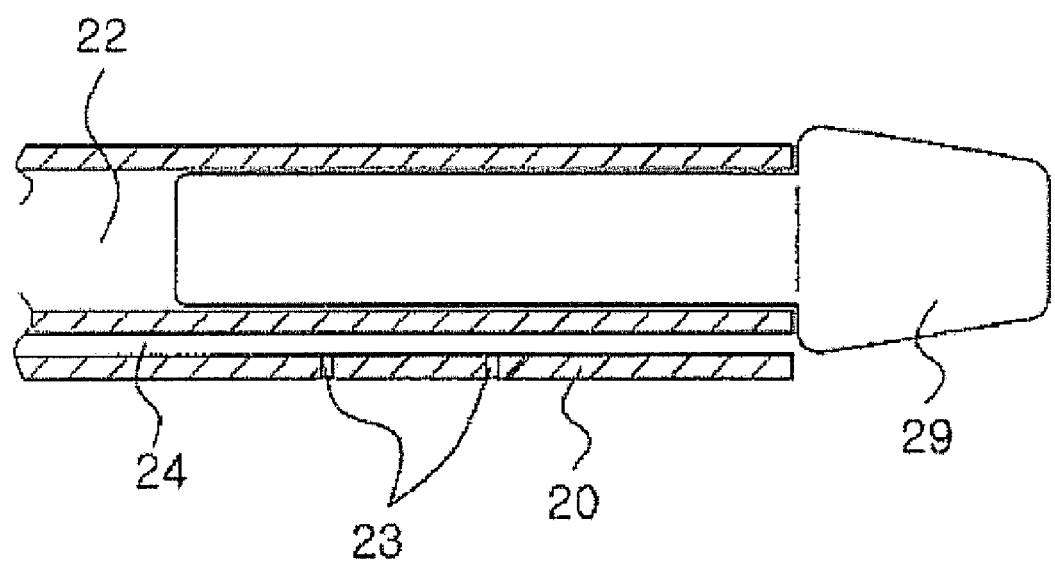
FIGS. 3A to 3C are sectional views respectively illustrating sequential steps of another conventional method for manufacturing a balloon catheter.
Figure 3B:
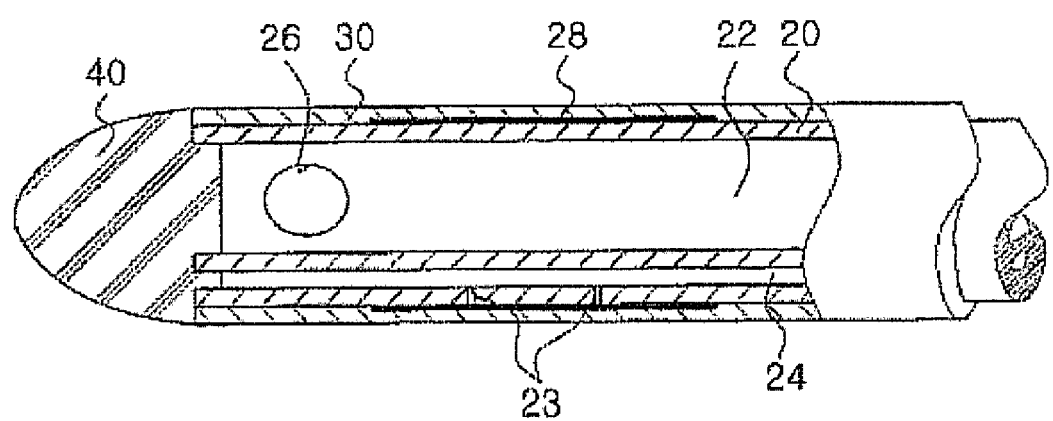
Figure 3C:
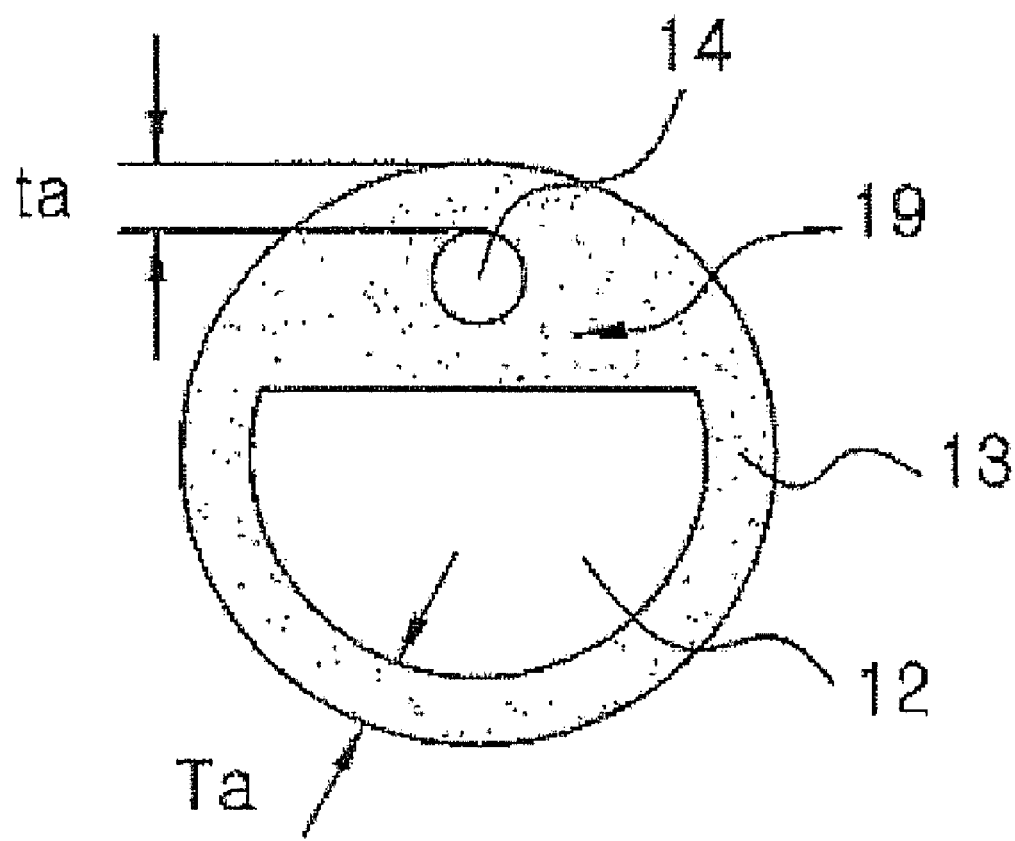

Each tube piece, which was completely formed with the tip, is perforated with a urine drainage hole (See reference numeral 170 in FIG. 2E), and then secondarily vulcanized at a temperature of 180° C. for two hours (Step ST-19).

As apparent from the above description, the present invention provides an apparatus and method for manufacturing a balloon catheter having the following effects.

Firstly, according to the present invention, a laser perforator is provided to project laser beams to an elongated non-vulcanized lumen tube such that inflation apertures having a predetermined area and length can be accurately perforated through the elongated non-vulcanized lumen tube in a non-contact manner during a primary extrusion process. Also, tube cutting positions can be accurately printed on the elongated non-vulcanized lumen tube at predetermined positions of the lumen tube in a non-contact manner simultaneously with the perforation of the inflation apertures, to achieve the accuracy of a following tube cutting process.

Secondly, the balloon catheter manufacturing apparatus of the present invention is designed such that the lumen tube is temporarily stationary dropped prior to entering a bond preventing agent applicator. This has the effect of compensating for a time delay between an intermittently performed bond preventing agent coating process and other foregoing and following processes.

Thirdly, according to the present invention, since liquid-phase silicon rubber is filled in an inflation lumen between a point just below the inflation aperture and a tip of each lumen tube piece corresponding to a desired balloon catheter by applying a negative pressure into the lumen tube piece, there is no risk of leakage of the liquid-phase silicon rubber regardless of the perforating direction of a urine drainage hole. This has the effect of enabling rapid manufacture of the balloon catheter, and minimizing maintenance labor costs.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. A method for manufacturing a balloon catheter comprising the steps of:
   primarily extruding an elongated lumen tube upward in a vertical direction by using a T-shaped die provided in a primary extruder,
   perforating inflation apertures through a non-vulcanized lumen tube at an interval of approximately 37 cm by using a non-contact type laser perforation device provided above the T-shaped die of the primary extruder, each inflation aperture having a width of 0.3 mm and a length of 2 to 3 mm, printing tube cutting positions on the non-vulcanized lumen tube at positions uniformly spaced apart from the inflation apertures by using a non-contact type printer provided above the laser perforator, simultaneously with the perforation of the inflation apertures, primarily vulcanizing the lumen tube, having passed through the perforation and printing processes, by using a primary vulcanizer provided above the printer, drawing the lumen tube by using a drawer including drawing and guide rollers, in order to prepare a primary curing of the lumen tube, stationary drooping the drawn lumen tube at a position just before a bond preventing agent applicator and intermittently feeding the lumen tube whenever the bond preventing agent applicator completes a foregoing bond preventing agent coating operation, uniformly coating a bond preventing agent layer on an outer peripheral surface of the lumen tube over the inflation apertures, drying the lumen tube, which was completely coated with the bond preventing agent layer using the bond preventing agent applicator, with hot air having a temperature of approximately 150° C., and intermittently transferring the dried lumen tube to a secondary extruder tube feeding roller, secondarily extruding the dried lumen tube by using the secondary extruder, when the dried lumen tube is fed to the second extruder after stationary dropping several times via the second extruder tube feeding roller, secondarily vulcanizing the secondarily extruded lumen tube by using a secondarily vulcanizing device provided below the secondary extruder, uniformly cutting the lumen tube, having passed through the secondary extrusion and vulcanization processes, to tube pieces by using a tube cutter based on the printed tube cutting positions of the lumen tube, each tube piece having a length suitable for forming a tip at one end thereof, forming a tip at one end of each tube piece by dipping the end of the tube piece into liquid-phase silicon rubber (LSR) while applying a negative pressure to an inflation lumen of each tube piece, and finish vulcanizing the tube pieces, each formed with the tip, at a temperature of approximately 125° C. for approximately 25 minutes, and perforating a urine drainage hole through each tube piece.

2. The method as set forth in claim 1, wherein an extruding speed of the secondary extrusion process is equal to or faster than that of the primary extrusion process.

* * * * *